(12) United States Patent
Peter et al.

(10) Patent No.: US 8,227,754 B2
(45) Date of Patent: Jul. 24, 2012

(54) OPTICAL IMAGING DETECTOR

(75) Inventors: Jörg Peter, Schriesheim (DE); Ralf Schulz, München (DE); Daniel Unholtz, Klein-Gerau (DE)

(73) Assignee: Deutsches Krebforschungszentrum Stiftung Des Oeffentlichen Rechts, Heildelberg (DE)

( * ) Notice: Subject to any disclaimer, the term of this patent is extended or adjusted under 35 U.S.C. 154(b) by 57 days.

(21) Appl. No.: 11/918,857

(22) PCT Filed: Apr. 10, 2006

(86) PCT No.: PCT/EP2006/061475
§ 371 (c)(1),
(2), (4) Date: Oct. 19, 2007

(87) PCT Pub. No.: WO2006/111486
PCT Pub. Date: Oct. 26, 2006

(65) Prior Publication Data
US 2009/0032714 A1 Feb. 5, 2009

(30) Foreign Application Priority Data
Apr. 19, 2005 (EP) .................................. 05008552

(51) Int. Cl.
*G01T 1/00* (2006.01)
*G01T 1/20* (2006.01)
(52) U.S. Cl. ..................................... 250/336.1; 250/368
(58) Field of Classification Search ............... 250/368, 250/336.1
See application file for complete search history.

(56) References Cited

U.S. PATENT DOCUMENTS

| 4,559,597 | A  | * | 12/1985 | Mullani ........................ 600/407 |
| 5,923,481 | A  | * | 7/1999  | Skidmore et al. .............. 359/819 |
| 6,987,274 | B1 | * | 1/2006  | Street et al. ................. 250/458.1 |
| 6,987,619 | B2 | * | 1/2006  | Kornrumpf et al. ........... 359/619 |
| 2002/0175267 | A1 | | 11/2002 | Watson et al. |
| 2003/0011701 | A1 | | 1/2003  | Nilson et al. |
| 2004/0214368 | A1 | | 10/2004 | Rhodes |
| 2004/0251419 | A1 | * | 12/2004 | Nelson et al. ............. 250/370.09 |

FOREIGN PATENT DOCUMENTS

| JP | 5-223738 A   | 8/1993 |
| JP | 2000-180365 A | 6/2000 |
| JP | 2001-108684 A | 4/2001 |

OTHER PUBLICATIONS

Collimator. (2009). In the Penguin Dictionary of Physics. Retrieved from http://www.credoreference.com/entry/pendphys/collimator, retreived Oct. 5, 2011.*

(Continued)

*Primary Examiner* — David Porta
*Assistant Examiner* — Carolyn Igyarto
(74) *Attorney, Agent, or Firm* — Birch, Stewart, Kolasch & Birch, LLP

(57) ABSTRACT

The invention relates to an optical imaging detector for fluorescence and bioluminescence imaging of an imaged object that can be used for tomographic imaging. The optical imaging detector comprises at least one micro-lens array with a plurality of micro-lenses. A photo detector can be located either in the focal plane of the micro-lens array or can be connected to the micro-lens array by a network of optical fibers and be located externally.

24 Claims, 10 Drawing Sheets

OTHER PUBLICATIONS

Collimation. (2008). In Mosby's Dental Dictionary. Retrieved from http://www.credoreference.com/entry/ehsdent/collimation, retreieved Oct. 5, 2011.*

Collimation. (2001). In Hargrave's Communications Dictionary, Wiley. Retrieved from http://www.credoreference.com/entry/hargravecomms/collimation, retreived Oct. 5, 2011.*

Collimate. (2007). In the American Heritage® Dictionary of the English Language. Retrieved from http://www.credoreference.com/entry/hmdictenglang/collimate.*

Collimate. (2007). In the Penguin English Dictionary. Retrieved from http://www.credoreference.com/entry/penguineng/collimate, retreived Oct. 5, 2011.*

Prout et al., "Detector concept for OPET, a combined PET and optical imaging system," 2003 IEEE Nuclear Science Symposium Conference Record/2003 IEEE Nuclear Science Symposium and Medical Imaging Conference, 2003, vol. 5, pp. 2252-2256, XP010737502, ISBN: 0-7803-8257-9.

Rannou et al., "Fully 3D System Model Estimation of OPET by Monte Carlo Simulation," Nuclear Science Symposium Conference Record, IEEE, 2004, pp. 3433-3436, XP010818678, ISBN: 0-7803-8700-7.

Rannou et al., "Investigation of OPET performance using GATE, a Geant4-based simulation softward," 2003 IEEE Nuclear Science Symposium Conference Record/2003 IEEE Nuclear Science Symposium and Medical Imaging Conference, 2003, vol. 5, pp. 2048-2052, XP010736016, ISBN: 0-7803-8257-9.

Weissleder, Nature Reviews Cancer, vol. 2, Jan. 2002, pp. 1-8, "Scaling Down Imaging: Molecular Mapping of Cancer in Mice".

English translation of Japanese Notice of Reasons for Rejection dated Jul. 26, 2011 for Japanese Application No. 2008-507050.

Zhang et al, "An Optical Real-time 3-D Measurement for Analysis of Facial Shape and Movement", Proceedings of the SPIE, vol. 5254, 2003, pp. 214-221, Bellingham, USA.

* cited by examiner

OPTICAL IMAGING DETECTOR

FIELD OF THE INVENTION

The present invention relates to an optical imaging detector and a method for fluorescence and bioluminescence imaging of an imaged object that can be used for tomographic imaging.

BACKGROUND OF THE INVENTION

The qualitative and quantitative acquisition of morphological, functional and biochemical parameters using imaging methods is the basis for a plurality of medical research and application areas. An overview over known imaging methods is given in "Scaling down imaging: Molecular mapping of cancer in mice", R. Weissleder, Nat Rev Cancer (1/2002), Volume 2, 1-8. Known imaging methods, which are applied e.g. in tumor research, include optical imaging techniques.

Such imaging methods for in-vivo examination known in the state-of-the-art are optical imaging techniques including fluorescence or bioluminescence imaging. In fluorescence imaging, light of one excitation wavelength illuminates the imaged object, resulting in a shifted emission wavelength that can be collected by a photo detector such as a CCD-camera. The imaged object is labelled for this purpose using a variety of fluorescence probes. Smart probes have been developed, that can be activated and detected only when they interact with a certain target, e.g. a small molecule, peptide, enzyme substrate or antibody. Bioluminescence imaging is used to detect photons that are emitted from cells that have been genetically engineered to express luciferases, catalysts in a light generating reaction, through the oxidation of an enzyme-specific substrate (luciferin). Unlike fluorescence approaches, the imaged object does not need to be exposed to the light of an external light source, the technique being based upon the internal light produced by the luciferases.

Planar optical imaging and optical tomography (OT) are emerging as alternative molecular imaging modalities, that detect light propagated through tissue at single or multiple projections. A number of optical-based imaging techniques are available, from macroscopic fluorescence reflectance imaging to fluorescence imaging/tomography that has recently demonstrated to localize and quantify fluorescent probes in deep tissues at high sensitivities at millimeter resolutions. In the near future, optical tomography techniques are expected to improve considerably in spatial resolution by employing higher-density measurements and advanced photon technologies, e.g. based upon modulated intensity light or very short photon pulses. Clinical optical imaging applications will require high efficient photon collection systems. OT has recently found applications, such as imaging of breast cancer, brain function and gene expression in vivo. Primary interest for using optical imaging techniques lies in the non-invasive and non-hazardous nature of optical photons used, and most significantly in the availability of activateable probes that produce a signal only when they interact with their targets—as compared to radiolabelled probes which produce a signal continuously, independent of interacting with their targets, through the decay of the radioisotope. In OT, images are influenced greatly by the spatially dependent absorption and scattering properties of tissue. Boundary measurements from one or several sources and detectors are used to recover the unknown parameters from a transport model described, for instance, by a partial differential equation. The contrast between the properties of diseased and healthy tissue can be used in clinical diagnosis.

In the state of the art optical imaging detectors are known either with (non-contact) CCD based or with (contact) fibre-optics based optical imaging designs.

The majority of existing optical imaging approaches are CCD based. CCDs (charge coupled devices) are charge coupled imaging sensors that serve for highly sensitive detection of photons. The CCD camera is divided into a multiplicity of small light-sensitive zones (pixels) which produce the individual points of an image. The grid of the pixels is formed by a circuit structure on a semiconductor crystal (usually silicon). The method of operation of the CCD camera is based on the liberation of electrons by impinging light in the semiconductor material. A photon falling onto a pixel liberates at least one electron that is held fixed by an electrical potential at the location of the pixel. The number of electrons liberated at the location of the pixel is proportional to the intensity of the light incident at that location. The number of electrons is measured in each pixel, with the result that an image can be reconstructed. CCDs should be cooled since otherwise more electrons would be read out which would not be liberated as a result of the light incidence but rather as a result of heating. In order to define an optical field-of view, the CCD detector is typically coupled to a lens.

However, almost all of the commercially available CCD based imaging designs generate only planar images of the integrated light distribution emitted from the surface of the imaged object, e.g. an animal. Market leader in the small animal optical imaging instrumentation arena is Xenogen Corp. Alameda, USA. The principle design of known CCD based optical imaging systems as used for in vivo fluorescence and bioluminescence imaging comprises a CCD camera, which is arranged at a certain distance to the imaged object (non-contact measurement) and aimed at this object in order to detect photons emitted from the object. Since CCD detectors need to be equipped with a lens which does impose a minimal focal length CCD cameras tend to be rather bulky instruments yielding large imaging compartments. If eventually used for tomographic imaging a CCD-based camera system needs to be rotated around the imaged object in order to collect projection views or a multitude of cameras needs to be used in parallel. In another potential application lens-based CCD camera systems of the prior art cannot be positioned within the field-of-view of another imaging modality with the purpose of dual-modality image acquisition such as positron emission tomography (PET) for simultaneous PET/optical imaging.

Known fibre optics based optical imaging designs are being used in a way that the fibre ending tips are placed in contact with the object to be imaged. One of the reasons is that a particular fibre ending tip does not have a distinct well-defined field of view which would allow for backtracking a photon's incoming direction. That means, for non-cylindrical imaging objects, such a mice, the object needs to be put into a cylindrical compartment which is filled with an appropriate liquid having specific optical properties. This is considered a significant drawback because of animal handling issues, experimental complexity and study management.

SUMMARY OF THE INVENTION

Therefore, the present invention is based on the object of avoiding the disadvantages of the prior art and particularly of providing a highly compact optical imaging detector with a high detection sensitivity, a high intrinsic spatial resolution and a high time resolution.

These objects are achieved by means of an optical imaging detector for fluorescence and bioluminescence imaging of an imaged object, the detector comprising at least one micro-lens array with a plurality of micro-lenses.

The micro-lenses of the micro-lens array are arranged to collimate light emitted from the imaged object onto a photo detector or (for certain applications) to project light towards the imaged object onto a part of the object to be imaged. By using an array of micro-lenses a position sensitivity can be achieved.

Each micro-lens has preferably a diameter in the range from 0.1 to 2 mm. By way of example with a lens diameter of 1 mm and an overall array size of 1 cm times 1 cm one micro-lens array assembles 100 lenses allowing for 1 mm spatially separated lens pitch—which subsequently corresponds to the intrinsic spatial detection resolution of the optical system. The micro-lens array can for example have a square, rectangular or hexagonal pattern. An optical collimator can be positioned in front or behind of each micro-lens array with the purpose of averting light cross-talk between individual micro-lens detector pairs. Such an optical collimator is preferably a multi-hole collimator which is adapted to the micro-lens array.

An optical imaging detector in the context of the present invention is a device capable of acquiring images of at least part of an imaged object by detecting fluorescent or bioluminescent signals (i.e. light) emitted from the imaged object. The imaged object can be any object known by those skilled in the art, which is accessible by optical imaging. Preferably the imaged object is an intact living organism like a small animal or sections of a human being such as breast or head.

According to one embodiment of the present invention the optical imaging detector is designed as a non-contact detector. The detector is not in contact with the imaged object, unlike the fibre-optics based optical imaging design with fibre ending tips being placed in contact with the object. The non-contact detector of the present invention has significant advantages in view of simplifying the handling of the imaged object (e.g. a living animal), reducing the experimental complexity and simplifying the study management.

The optical imaging detector according to the present invention preferably comprises at least one photo detector.

A photo detector is a sensor, which is arranged to detect photons emitted from the imaged object. The photo detector comprises for example at least one CCD camera or at least one photo diode. Preferably the at least photo detector is a position sensitive photo detector, which detects photons and the position of their entering the photo detector. Examples for position sensitive photo detectors are a CCD (charge-coupled device) based detector, an APD (avalanche photo diode) array, a photo diode array or a CMOS (complementary metal-oxide semiconductor) sensor. An APD array or a photo diode array contains a plurality of APDs or photo diodes respectively, which is arranged in an array.

A CMOS (complementary metal oxide semiconductor) sensor is an active pixel sensor, which includes an array of photo sensitive diodes, one diode within each pixel. Each pixel has its own amplifier, allowing pixels to be read individually which leads to the position-sensitivity of the CMOS sensor.

Preferably the optical imaging detector according to the present invention further comprises a photo detector which is located at the focal plane of the micro-lens array or which is connected to the micro-lens array via optical fibres.

In one preferred embodiment of the present invention, each micro-lens is connected to an optical fibre. The advantage of this embodiment is that each fibre coupled photo detector has its own individual dynamics. Preferably each micro-lens is connected to a photo detector element, e.g. a photo diode, or to a light source via an optical fibre. These optical fibres can take on two different purposes: either the light collected by the micro-lenses will be tracked through the fibres to the photo detector element for detection or light from the light source (e.g. laser diode) is tracked through the fibres to the imaged object, e.g. for fluorochrome excitation.

In another preferred embodiment of the present invention, the at least one position sensitive photo detector is positioned at a focal plane of one of the micro-lens arrays. In this case, no optical fibres are needed to transfer photons from the micro-lenses of the micro-lens array to the photo detector, thus simplifying the detector construction.

One immediate advantage of using optical detectors with micro-lens arrays, as compared to CCD cameras, lies in the locally adaptive dynamic range of the optical system, if partitioned photo detectors such as fibre coupled photo detector arrays are used that allow for individual detector element read-out. As a consequence, the dynamic range of the over-all tomographical optical system is greatly improved, allowing for fast (parallel) fully tomographic projection data acquisition, independent of laser excitation position and pattern. The use of optical imaging detectors with photo detectors coupled to the micro-lens array's focal plane has the advantage that detection sensitivity as well as intrinsic spatial resolution (the two main characteristics of static imaging) are higher than for fibre-based systems. Furthermore, time resolution (another very important property) is higher than achievable with a rotatable CCD camera detector system. Diametric sampling efficiency is superior and the described optical imaging detector of the present invention can be significantly smaller in its physical dimension than e.g. lens-mounted photo detectors such as CCD cameras allowing for system integration. This is particularly characteristic for a preferred embodiment of the present invention where photo detectors are directly positioned and aligned at the micro-lens array's focal plane. Micro-lens arrays are known in prior art and have so far been used as coupling elements between optical fibre bundles, for the formation of two-dimensional light fields or for light field photography.

With the optical imaging detector for fluorescence and bioluminescence imaging according to the invention it is possible to perform simultaneous fully 3-dimensional acquisition of in vivo distributions of optical markers/probes, which neither requires the detector to be in contact with the image object, nor a bulky lens-equipped fully rotatable CCD camera. The latter cannot simultaneously acquire projection views at a comparable high number of views due to the physical size of the imager. Furthermore, the optical detector assembly constitutes a very thin detector that can be used within space-limited environments. One particular application is the integration of such an optical imaging detector within a small animal PET scanner, which is not possible with a lens-equipped camera.

The optical imaging detector according to the present invention can comprise at least one light source arranged to illuminate at least part of the imaged object. For example in fluorescence imaging the at least one light source illuminates at least part of the imaged object with light of an excitation wavelength in order to excite fluorescence probes within the imaged object, resulting in the stimulated emission of light with a shifted wavelength.

The optical imaging detector can further comprise at least one filter on front of each micro-lens array for filtering out light of the at least one light source. Such a filter can be provided e.g. for the purpose of filtering out laser excitation light, when the detector is used for fluorescence imaging. For bioluminescence imaging no filter is needed. The filter is preferably removable or replaceable. Different filters can be used for different optical probes/markers needing excitation light of specific wavelength which require appropriate filter arrangements.

The optical imaging detector according to the invention can be used to image an object either from a single view (planar projection) or in tomographic manner. For tomographic imaging two approaches exist: either an optical imaging detector in the form of a single imaging device capable of acquiring a single view is rotated 360° around the imaged object while acquiring data or an optical imaging detector comprising a number of similar imaging devices capable of acquiring individual single views, which devices are allocated in a cylindrical assembly around the long-axis of the imaged object to acquire projection data simultaneously. In either approach the individually acquired views are used to mathematically calculate tomographic slices through the imaged object. An optical imaging detector in the form of a single imaging detector, taken from a tomographic design concept can also be used to image an object in planar mode. Tomographic imaging can only be performed if light (i.e. in this application preferably photons emitted by fluorescent or bioluminescent probes) can penetrate the object to be imaged. Tomographic imaging yields more information than planar imaging and is particularly useful in biomedical applications if one wants to assess functional and molecular processes in vivo.

Preferably the optical imaging detector according to the invention comprises at least two opposed micro-lens arrays. Thereby photons emitted by the imaged object in opposite directions can be detected. In a preferred embodiment of the present invention a plurality of planar or curved micro-lens arrays is arranged in a ring structure. The optical imaging detector comprising micro-lens arrays arranged in a ring structure has the advantage (for example over a CCD based system) of allowing the complete and three-dimensional tomographic optical imaging of an object with an improved dynamic range (sensitivity).

The present invention therefore also refers to a non-contact three-dimensional optical imaging method, wherein imaging data of the imaged object is acquired solely by an optical imaging detector according to the present invention (comprising micro-lens arrays arranged in a ring structure, which are coupled to photo detectors) with the purpose of imaging optical photons emitted from the imaged object, the micro-lens array ring structure surrounding the imaged object.

In a preferred embodiment of the present invention, the optical imaging detector is mounted on a rotatable gantry. Preferably, the gantry (and with it the detector) is rotatable (e.g. around a longitudinal axis of the imaged object) and translatable (e.g. along the longitudinal axis of the imaged object). The gantry with the optical imaging detector can be rotatable around its vertical and/or its longitudinal axis. The gantry can be rotatable for 360° to allow an arbitrary radial positioning of the optical imaging detector and to allow tomographic imaging. A gantry holding two opposing micro-lens arrays, one on each side of the imaged object, can e.g. rotate at 180° single-step mode around the imaged object during data acquisition in order to acquire tomographic data.

The optical imaging detector according to the invention is preferably radially relocatable in relation to the imaged object. Thereby the system can be adapted to different objects to be imaged. For example two opposed detector blocks, each comprising a micro-lens array, can be adjusted in their separation (being radially relocatable) in order to optimize detection efficiency with different-sized imaged objects (e.g. laboratory animals).

The present invention can be applied in medical imaging in general. Arrays of major applications can be positioned in molecular biology, genetic research, oncology, cancer research, pharmacology and drug research. Primary tasks and intended applications for the optical imaging detector according to the present invention are as follows: to image specific cellular and molecular processes, e.g. gene expression, or more complex molecular interactions such as protein-protein interactions, to monitor multiple molecular events simultaneously, to track single or dual-labelled cells, to optimize drug and gene therapy, to image drug effects at molecular and cellular level, to assess disease progression at a molecular pathological level, to create the possibility of achieving all of the above goals of imaging in a single, rapid, reproducible and quantitative manner. For further applications specific use of the present invention is to monitor time-dependent experimental, developmental, environmental and therapeutic influences on gene products in the same animal (or patient), to study the interaction of tumour cells and the immune system, to study viral infections by marking the virus of interest with a reporter gene, and others. There is also an enormous clinical potential for the non-invasive assessment of endogenous and exogenous gene expression in vivo (gene (DNA), message (RNA), protein, function), for imaging receptors, enzymes, transporters, for novel applications in basic and translational research (gene therapy), for early detection of disease, for guidance of therapeutic choices, for monitoring drug action, for aid of pre-clinical drug development, for non-invasive and repetitive monitoring of gene therapy and for optimizing clinical trials of human gene therapy.

The present invention is explained in greater detail below with reference to the drawing.

DESCRIPTION OF THE FIGURES

FIG. 1 shows schematically a first embodiment of an optical imaging detector according to the present invention. The first embodiment shown in FIG. 1 and described in the following is the best mode for carrying out the invention.

Figure 1:
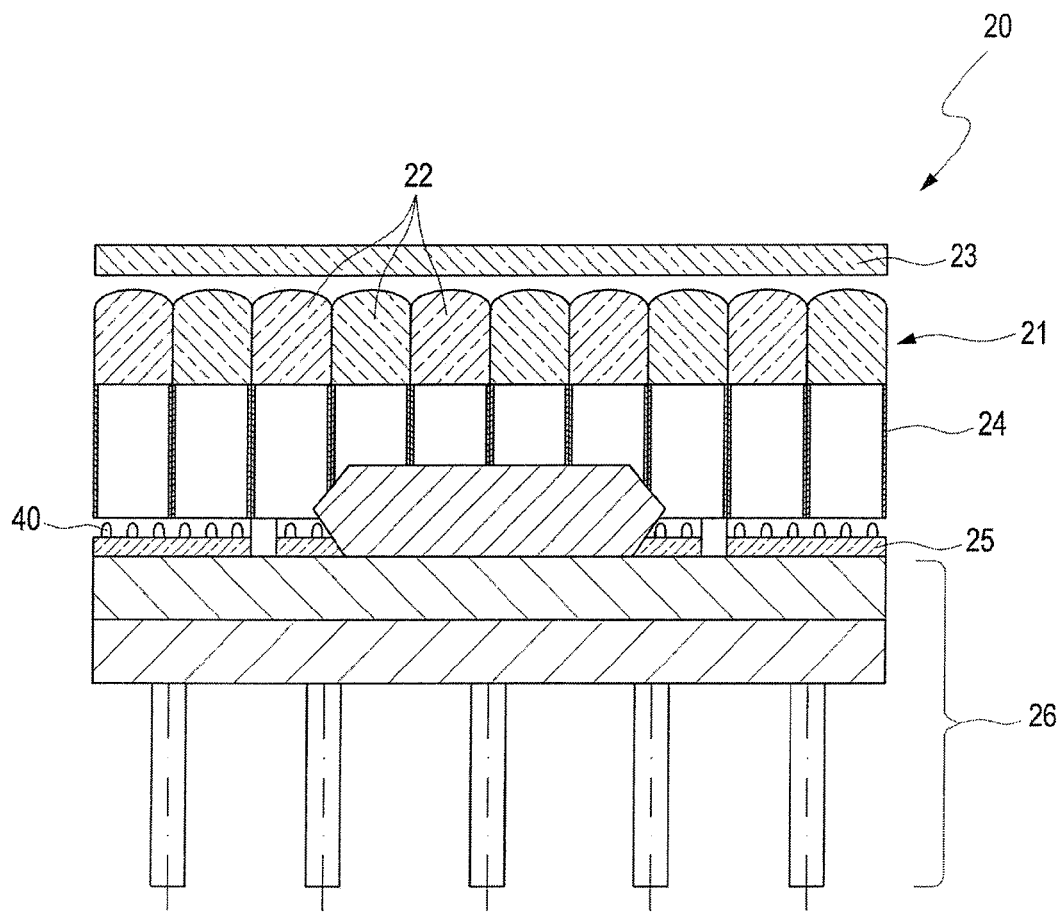
FIG. 1 shows schematically a first embodiment of an optical imaging detector according to the present invention.

The figure shows a cross-section of a detector block 20. An optical imaging detector according to the present invention can comprise one such detector block 20 or a plurality of detector blocks 20. The detector block 20 contains a micro-lens array 21 with a plurality of micro-lenses 22, which are arranged in a two-dimensional lattice. Preferably all micro-lenses 22 have identical geometrical and optical properties, but if necessary for an application, these properties can vary with reference to the individual micro-lenses 22 of the micro-lens array 21. The diameter of the micro-lenses 22 is chosen based upon application-required spatial resolution properties. Exemplarily lens diameters of 0.48 mm and of 1.0 mm have been selected for two different applications.

The detector block 20 further comprises a filter 23 positioned in front of the micro-lens array 21. The filter 23 is that part of the detector block 20, which is closest to the imaged object (not shown). The micro-lens array 21 is mounted behind the filter 23 in radial extension to the imaged object. The filter 23 is provided e.g. for filtering out laser excitation light when the detector block 20 is used for fluorescence imaging. The filter 23 is not needed for bioluminescence imaging.

On the other side of the micro-lens array 21 an optical collimator 24 is positioned between the micro-lens array 21 and the photo detector 26. This photo resist collimator 24 has preferably a hole order and pitch similar to the micro-lens order and pitch of the micro-lens array 21. The collimator 24 is provided to avoid cross-talk between individual fields-of-view of the micro-lenses 22. The thickness of the collimator 24 in radial extension depends upon the space between the back facing surface of the micro-lens array 21 and the virtual focal plane of the micro-lenses 22.

Next to the collimator 24 a large-field photo detector 25 is mounted. The photo detector 25 is positioned at the focal plane of the micro-lens array 21. This photo detector 25 can be a CCD based detector, an APD array, a photo diode array, a CMOS sensor and any other position sensitive light detector. Preferably the photo detector 25 is a CMOS sensor, which shows many advantages in view of its performance (sensitivity, noise characteristics, time resolution, etc.) and in view of its cost. The photo detector 25 transforms the incoming light, which passes the filter 23, the micro-lens array 21 and the optical collimator 24, into an electrical signal.

The micro-lenses 22 of the micro-lens array 21 are distanced by a certain pitch, which should be equal to or a multitude of the photo detectors 25 pitch in order to avoid Moiré artefacts in the acquired image. Exemplarily in one experimental setup micro-lenses 22 are used with a lens diameter equal to lens pitch of 0.48 mm. The pitch of pixels 40 of an employed CMOS sensor is chosen to be 1/10 of this (0.048 mm). The photo detector 25 is a position sensitive sensor consisting of a two-dimensional lattice of individual sensor elements 40.

The overall dimensions of all previously described detector parts 21, 23, 24 and 25 used for image formation and detection should be equal. That is, if the size of a micro-lens array 21 is chosen to delineate a field-of-view of 1 cm×1 cm so should be the sizes of the sensor 25, collimator 24 and filter 23 as well. This is, however, not required for the sole purpose of detection. In principle, detector parts 21, 23 and 24 might be replaceable allowing for modification of imaging characteristics. If additional electronics parts and signal transmission elements 26 are necessary, as in the shown CMOS design, these should be placed outside of the detector's field-of-view.

The detector block 20 of FIG. 1 can either be used for two-dimensional (i.e. planar) or, if assembled or rotated in a certain manner, for fully 3-dimensional tomographic imaging. In most application scenarios a detector block 20 is positioned at a certain distance, but not in contact with the imaged object, with its micro-lens array detector surface oriented orthogonal to the imaged object or portions thereof. The sensitive size of such a detector block 20 can be selected arbitrarily (being constrained by technological processes) but should be governed by the size of the imaged object or portions of it. Exemplarily the detector block size is chosen to be 5 mm (transaxially)×70 mm (axially) such that a whole mouse (in axial extension) can be imaged by view. In another specific application the detector size is chosen with 25 mm (transaxially)×70 mm (axially). In this case the detector's field-of-view covers an entire mouse.

Figure 2:
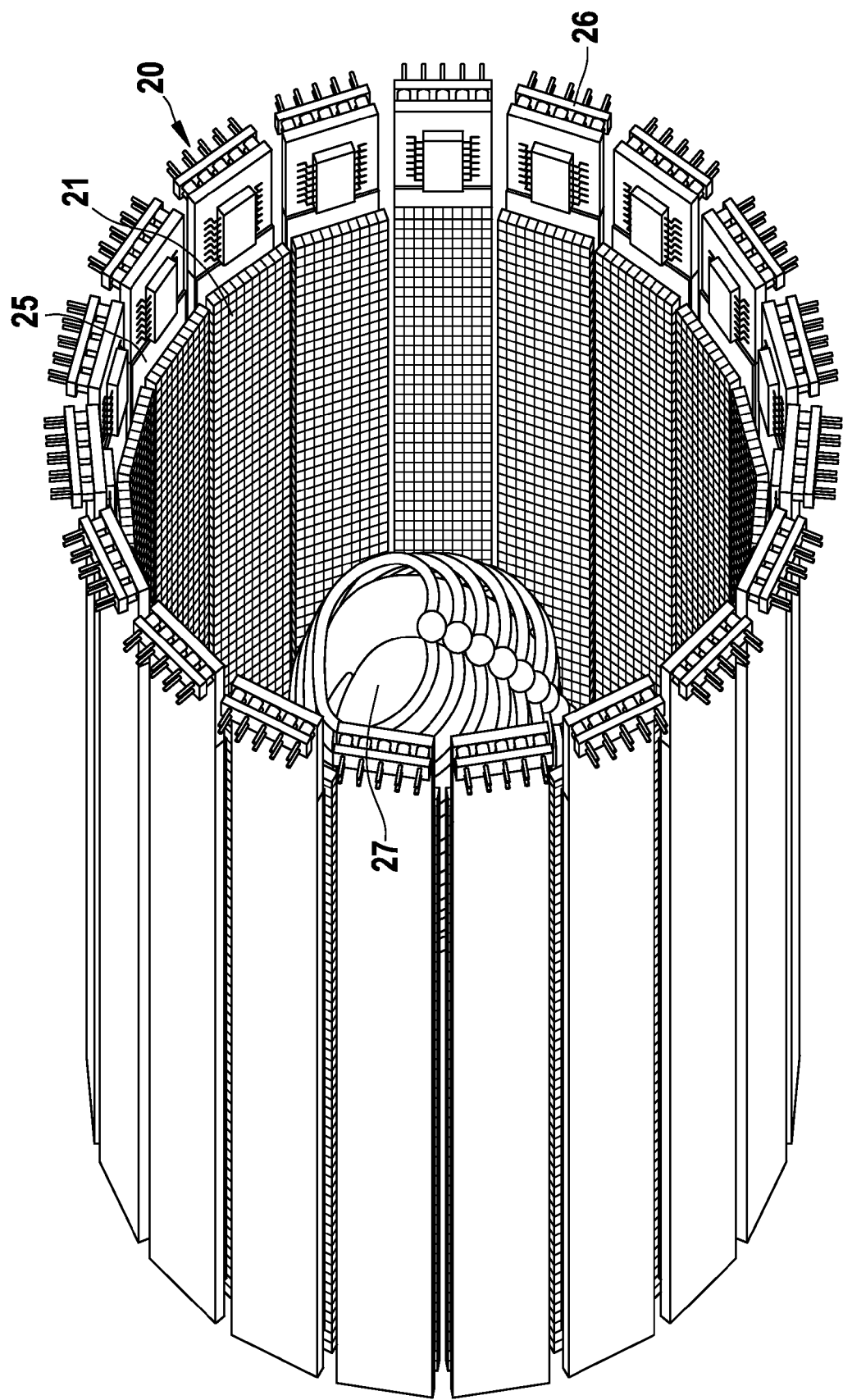
FIG. 2 shows schematically an optical imaging detector according to the present invention with a plurality of detector blocks according to FIG. 1 arranged in the ring structure.

FIG. 2 shows schematically an optical imaging detector according to the present invention with a plurality of detector blocks according to FIG. 1 arranged in a ring structure.

A multitude of the previously described detector blocks 20 is arranged in a ring structure surrounding an imaged object 27, in this case a mouse phantom. Each detector block 20 comprises a micro-lens array 21 (without filter), a collimator (not shown), a photo detector 25 and electronics parts and signal transmission elements 26. The shown optical imaging detector can be used for tomographic bioluminescence imaging.

Figure 3:
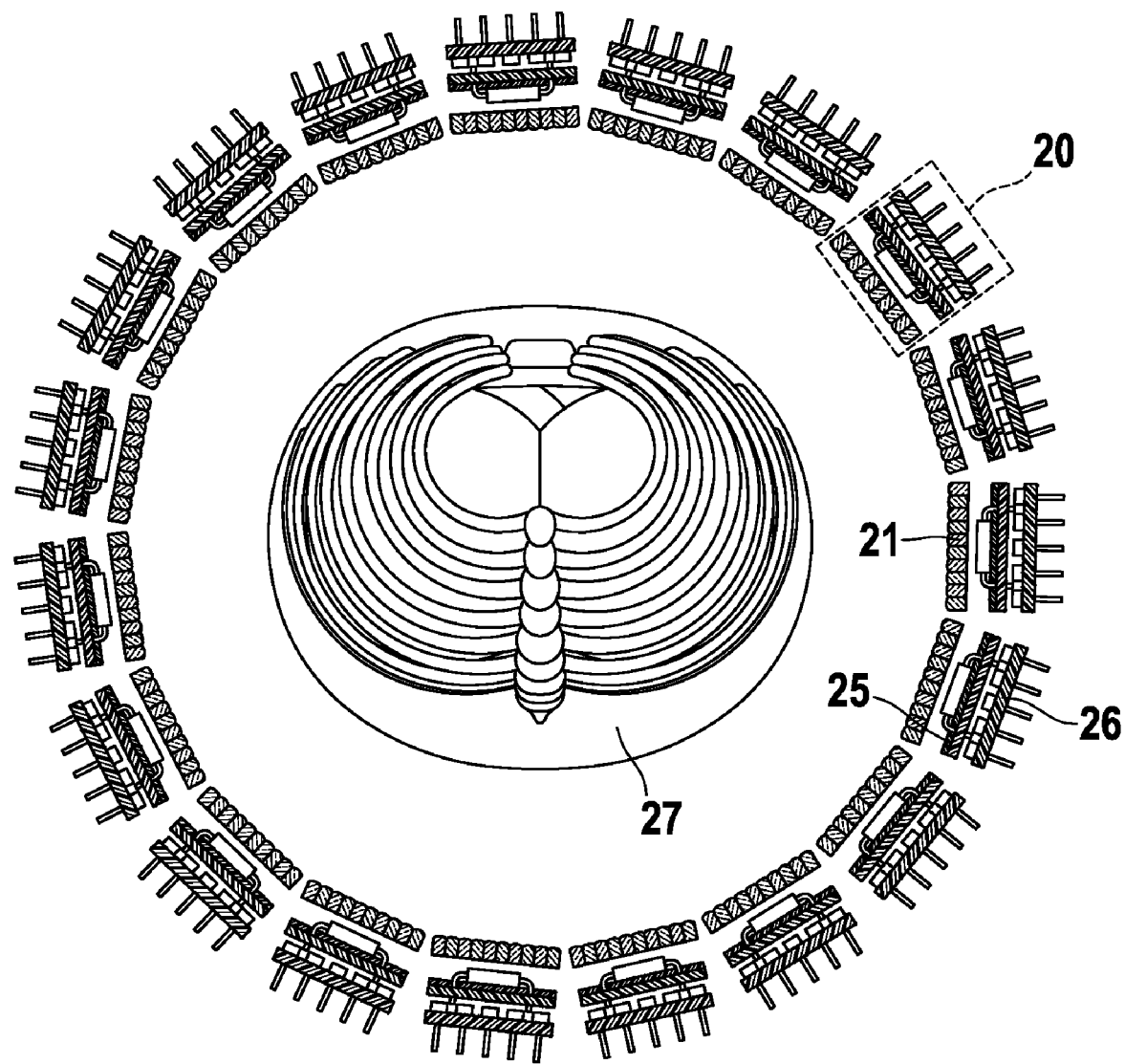
FIG. 3 shows schematically a cross-section of the optical imaging detector according to FIG. 2.

FIG. 3 shows schematically a cross-section of the optical imaging detector according to FIG. 2.

Figure 4:
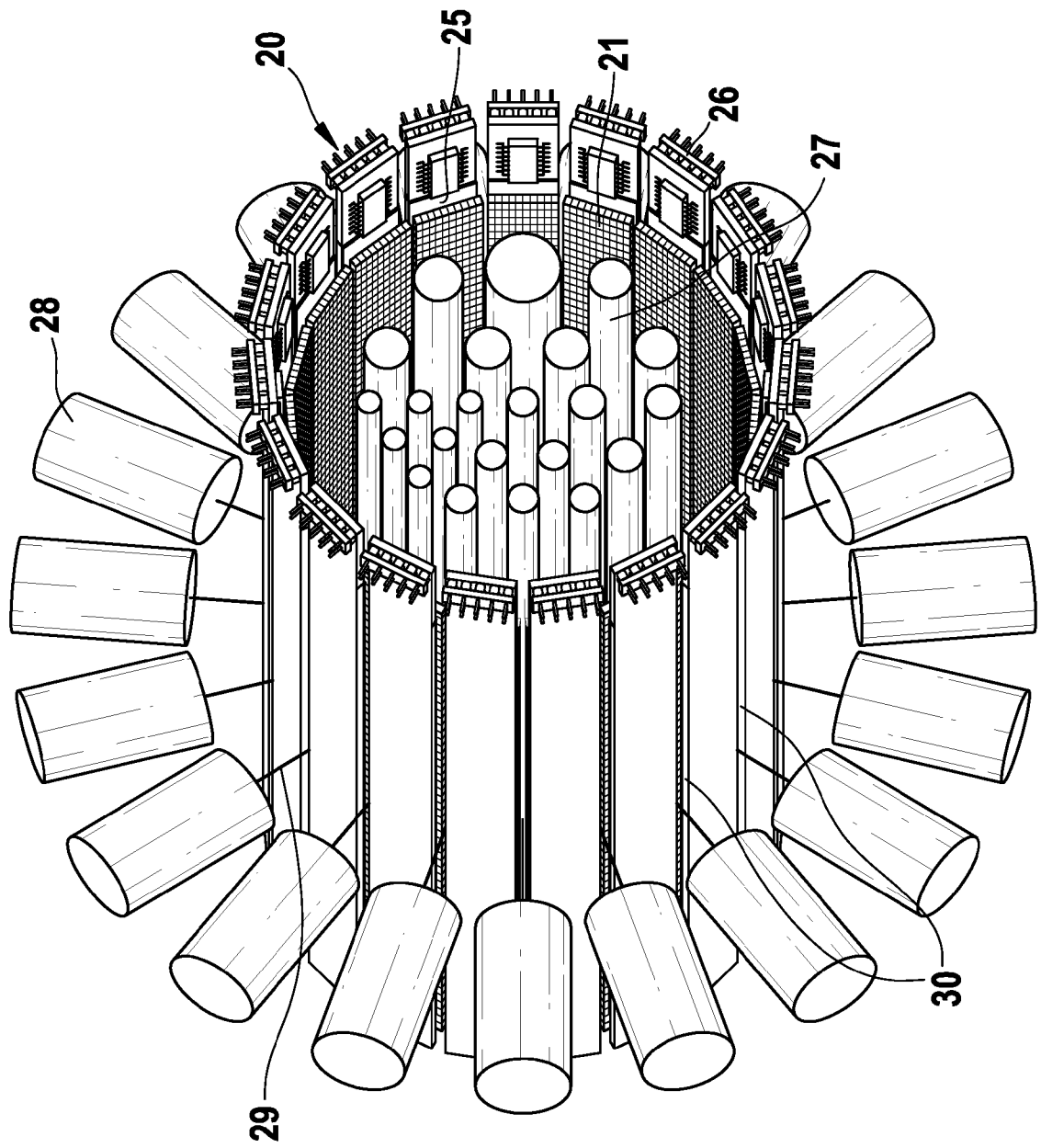
FIG. 4 shows schematically an optical imaging detector according to the present invention with a plurality of detector blocks and light sources arranged in a ring structure.

FIG. 4 shows schematically an optical imaging detector according to the present invention with a plurality of detector blocks and light sources arranged in a ring structure.

A multitude of the previously described detector blocks 20 according to FIG. 1 is arranged in a ring structure surrounding an imaged object 27, in this case a Derenzo phantom. Each detector block 20 comprises a micro-lens array 21, a filter (not shown) a collimator (not shown), a photo detector 25 and electronic parts and signal transmission elements 26. A plurality of light sources 28 arranged in a ring structure surrounds the ring structure of detector blocks 20. The light 29 of the light sources 28 illuminates the imaged object 27 through gaps 30 between the detector blocks 20. The shown optical imaging detector can be used for tomographic fluorescence imaging.

An application-specific light source 28 to excite a fluorescence probe might be one of the following: a single or multitude of radially relocatable lasers (laser diodes) with selectable wavelength and power. In FIG. 4 the number of lasers equals the number of detector blocks 20. Detectors and lasers are preferably mounted on a rotatable and axially translatable common gantry (not shown). Alternately a single laser (or other light source 28) with selectable wavelength and power can be placed outside the detector block assembly while light is transmitted via fibre optics, and possibly splitted using optical switches, to the imaged object 27, or a single or multitude of bright-field light sources with selectable wavelength and power in form of thin tubes can be oriented parallel to the object's 27 long axis and placed at the gaps 30 between the detector blocks 20. The latter design can have a fan beam collimator per light source 28 to limit the light source's 28 beam pattern towards the imaged object 27, avoiding direct illumination of the photo detector 25 behind its filter 23. The entire optical imaging detector assembly is preferably rotatable around the long axis of the ring structures. Also feasible is the individual rotation of the detector blocks themselves. The rotation improves spatial sampling. Without this rotational feature the number of transaxial laser positions and detector views is fixed with the number of excitation lasers and detector elements, respectively (20 in the shown example). Rotation is only needed for the arc length of 360° divided by the number of lasers and/or detectors, respectively.

In order to excite/illuminate the object at any location along its axial extension the laser(s) can also be translated along the axis of rotation.

Figure 5:
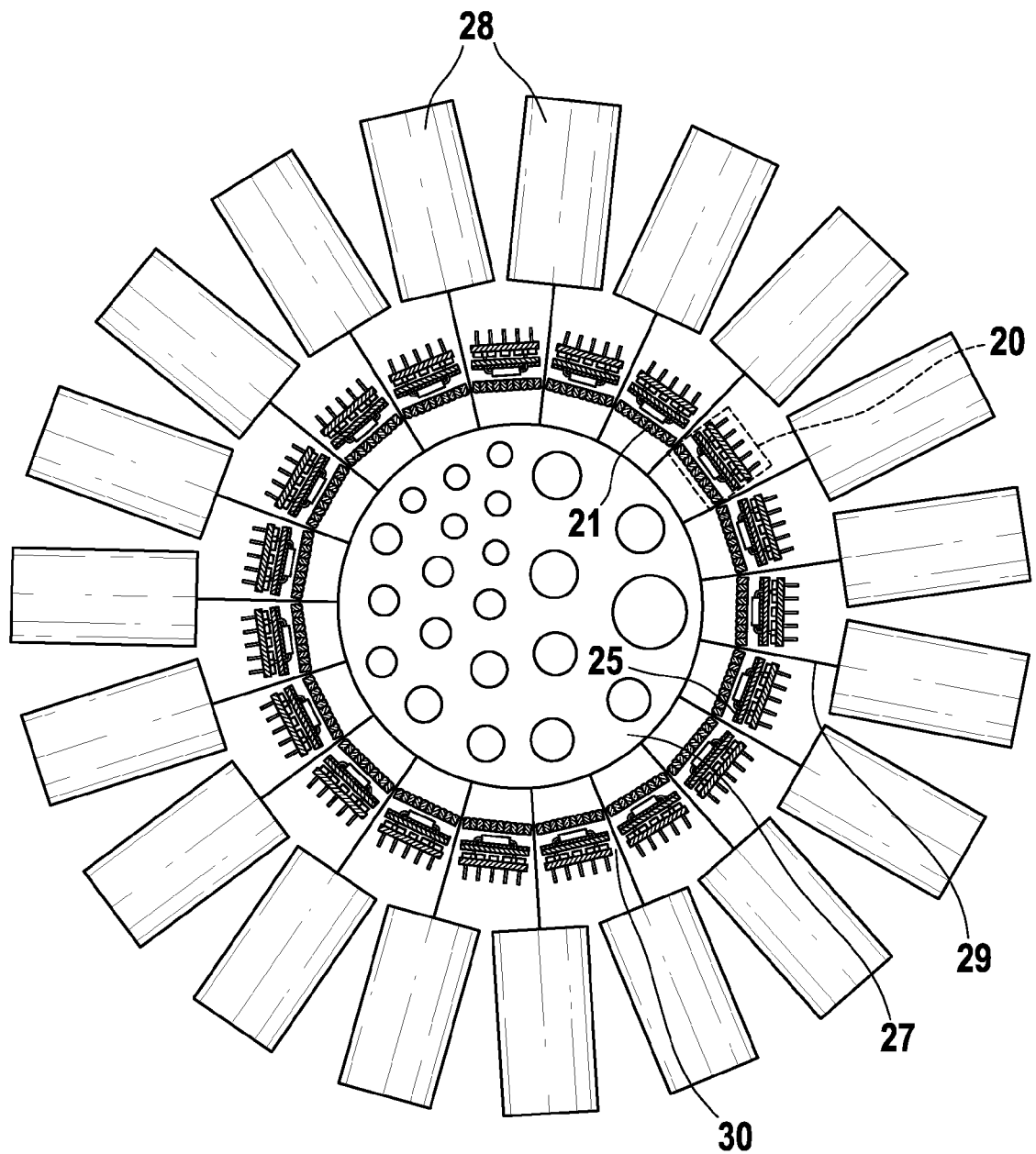
FIG. 5 shows schematically a cross-section of the optical imaging detector according to FIG. 4.

FIG. 5 shows schematically a cross-section of the optical imaging detector according to FIG. 4.

Figure 6:
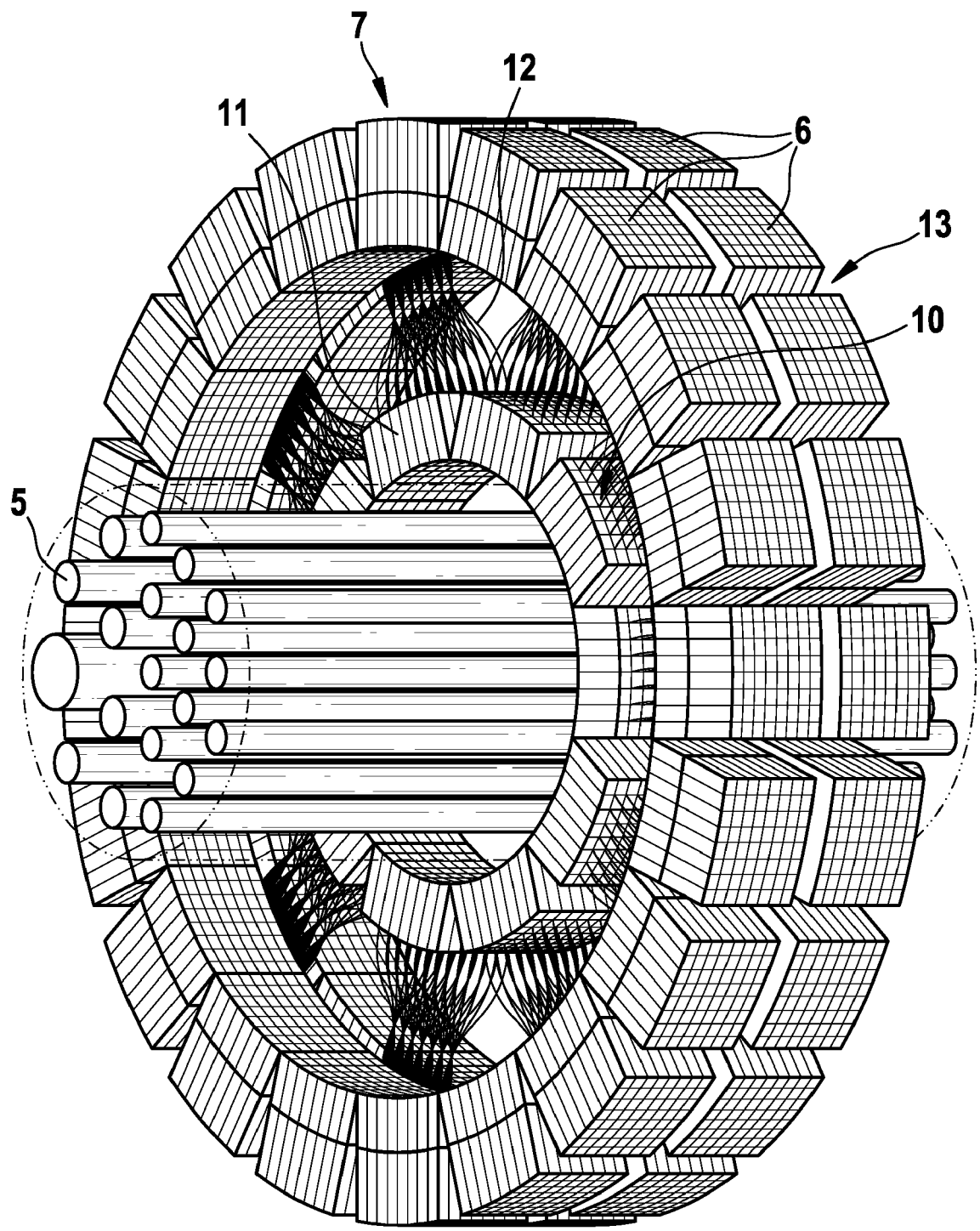
FIG. 6 shows schematically a dual-modality imaging system with a ring of γ-ray detector arrays surrounding a ring of micro-lens arrays of a second embodiment of an optical imaging detector according to the present invention.

FIG. 6 shows schematically a dual-modality imaging system with a ring of γ-ray detector arrays surrounding a ring of micro-lens arrays of a second embodiment of an optical imaging detector according to the present invention.

This dual-modality imaging system comprises a PET scanner with a plurality of gamma-ray detector arrays 6, which are arranged in a ring form 7, surrounding the imaged object 5. The dual-modality imaging system further comprises a plurality of micro-lens arrays 10, each containing a plurality of micro-lenses. The plurality of micro-lens arrays 10 is arranged in a ring structure 11, surrounding the imaged object 5, the ring structure 11 being arranged within the ring form 7 of gamma-ray detector arrays 6. Therefore, the micro-lens arrays 10 form the system's inner (optical) ring. This embodiment of a dual-modality imaging system uses a radial cylindrical lattice of micro-lens arrays, which are mounted in front of the PET detector blocks. The PET detector blocks 6 for the detection of high energy (511 keV) isotopic photons are distanced in radial extension to the micro-lens arrays 10 of the optical detectors. Although the PET detectors 6 can consist of state-of-the-art detection materials (pixelized crystals optically mounted to position-sensitive photo multiplier tubes), they can be custom-manufactured to reflect the block geometry specified for the micro-lens array blocks 10. Even though parts of the optical detection system (micro-lens array 10, optical fibres 12, fibre mounting plates) are within the field-of-view of the PET sub-system, the optical system is insensitive for isotopic photons and the PET system is (nearly) unaffected by the optical parts as the high energy photons penetrate the incorporated materials with very small attenuation and scattering. The optical micro-lens system is "stripping away" optical photons while they have no effect on isotopic photons. Optical fibres 12 are attached to the micro-lenses, leading to the outside of the ring form 7 through spaces 13 between the gamma-ray detector arrays 6. The network of optical fibres bundles integrated into the system can be used to guide laser excitation light from an external multi-wavelength laser (not shown) to the imaged object 5. Individual fibres 12 can be activated selectively, allowing for a variety of laser excitation patterns.

The network of optical fibres bundles integrated into the system can also be used to guide emitted light collimated by the micro-lenses of the micro-lens arrays 10 from the imaged object 5 to external photo detectors, e.g. photo diode arrays, for detection (not shown). These photo detectors are part of the optical imaging detector according to the present invention. The optical fibres 12 are connected to the focal points of the micro-lenses. They are fixed by a multihole plate in this position. Due to the flexible fibres 12 it is not required that the photo detector geometry (photo element size and pitch) of the optical imaging detector according to this embodiment of the present invention is similar to the micro-lens geometry.

The number of micro-lens arrays 10 per ring structure 11 is defined by the size of the imaged object 5 and the size of the lens array 11. Considering exemplarily the geometry of a small animal (mouse) system, for a transaxial object diameter of 3 cm and a given lens array size of 1 cm×1 cm, the ring consists of ten radially allocated lens arrays. Micro-lens arrays are available commercially (SUSS MicroOptics SA, Neuchatel, Switzerland) and are currently manufactured from 0.5 cm to 1.27 cm in square size. Each lens array consists of a square, rectangular or hexagonal pattern of packed micro-lenses which are each manufactured with a radius in the range of 0.1 mm to 2 mm. The micro-lens arrays 10 and the gamma-ray detector array 6 can be mounted on a common rotatable and translatable gantry (not shown), which allows for unconstrained arbitrary orbital positioning of the optical detectors and optical fibre bundles.

Micro-lens arrays are available from SUSS MicroOptics SA, Neuchatel, Switzerland. Optical fibres, lasers and CCD cameras are available from several manufacturers (Roper Scientific, Inc., Duluth, Ga., and others).

Integrated into the system as shown in FIG. 6 are also (not shown) axially moveable optical filters for wave-length separation. In case of non-tomographic optical imaging, the operator will position the laser/detector blocks at an optical orbital position for light measurements depending on the present optical probe distribution within the object.

Figure 7:
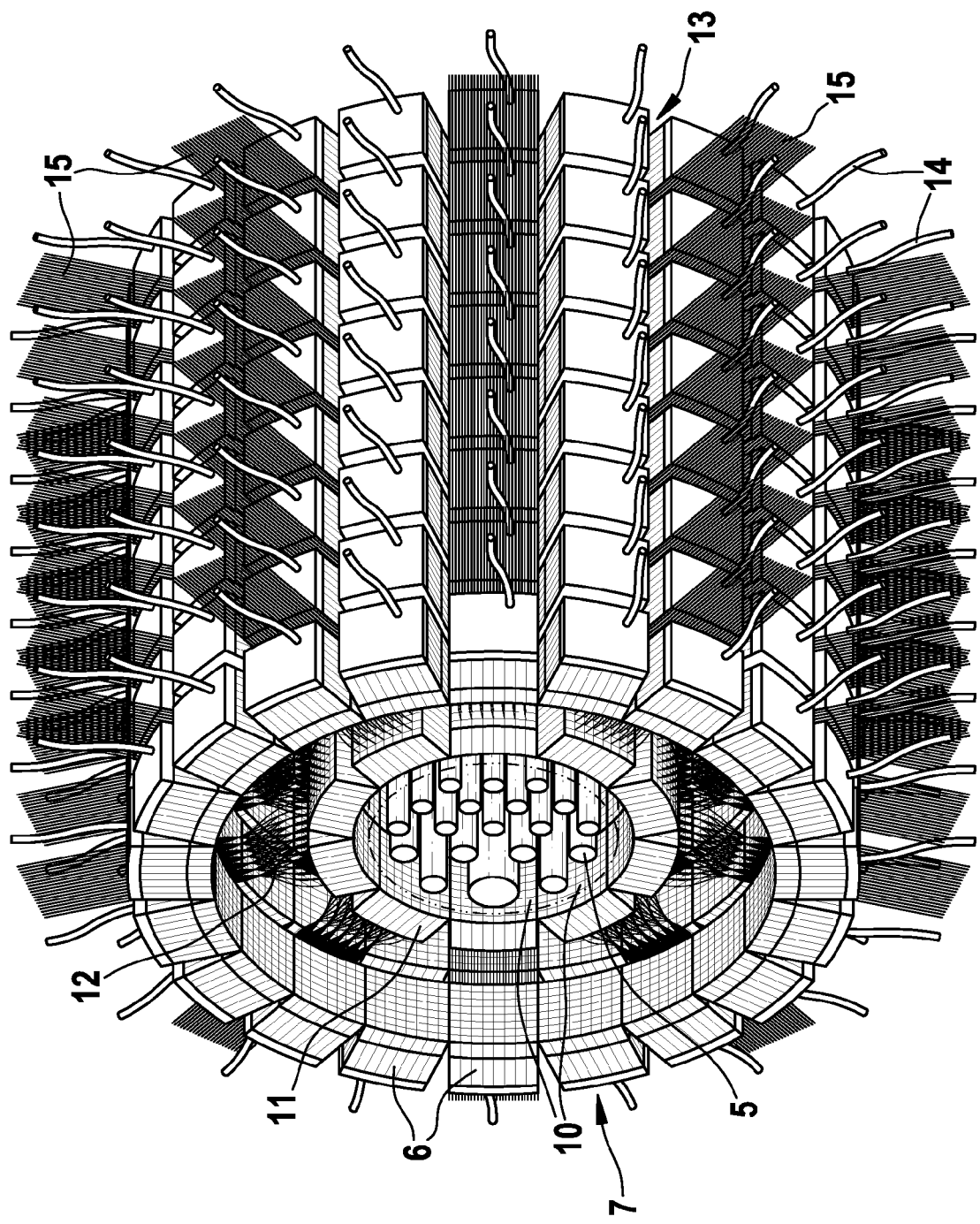
FIG. 7 shows a variation of the embodiment according to FIG. 6 with a larger number of micro-lens arrays.

FIG. 7 shows a variation of the embodiment according to FIG. 6 with a large number of micro-lens arrays.

The imaged object 5 is along its whole length surrounded by a ring structure 11 of micro-lens arrays 10, which is arranged within a plurality of gamma-ray detector arrays 6 in ring form 7. Six rings of twenty gamma-ray detector arrays 6 each are mounted in a row. Each gamma-ray detector array 6 has an electrical connection 14. The optical fibres 12 which are attached to the micro-lens arrays 10 exit the PET scanner through the spaces 13 between the gamma-ray detector arrays 6 in the form fibre bundles 15 and are e.g. connected to photo detectors (not shown). The ring structure 11 is formed by eight rings of ten micro-lens arrays 10 each.

Figure 8:
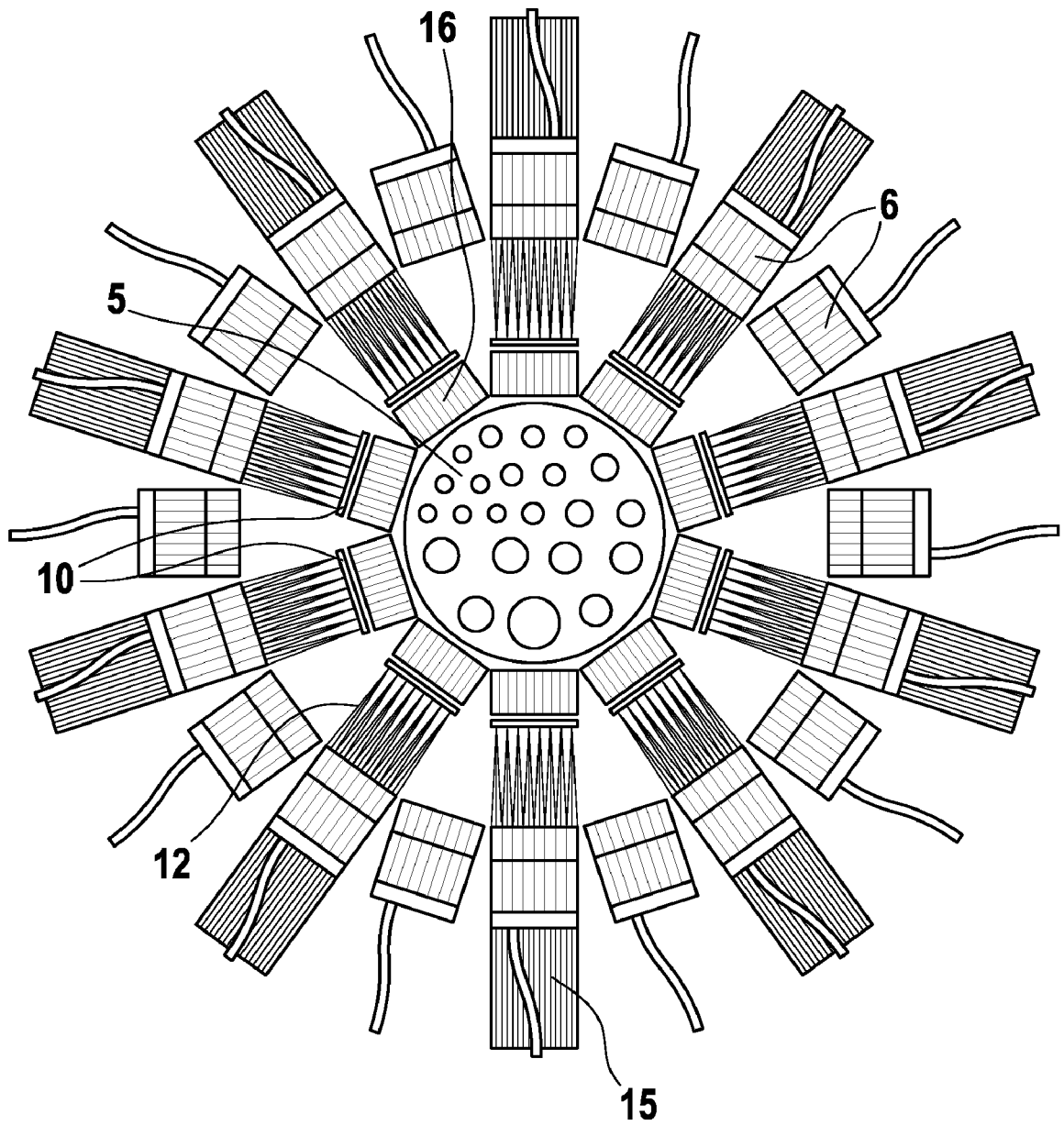
FIG. 8 shows a cross-section of the embodiment of FIG. 6.

FIG. 8 shows the cross section of the embodiment as shown in FIG. 6.

In this illustration, the arrangement of the components of the dual-modality imaging system with the optical imaging detector according to the present invention (micro-lens arrays 10, optical fibres 12, photo detector (not shown)) around the imaged object 5 can be seen. The system further comprises an optical collimator 16 in front of each micro-lens array 10.

Figure 9:
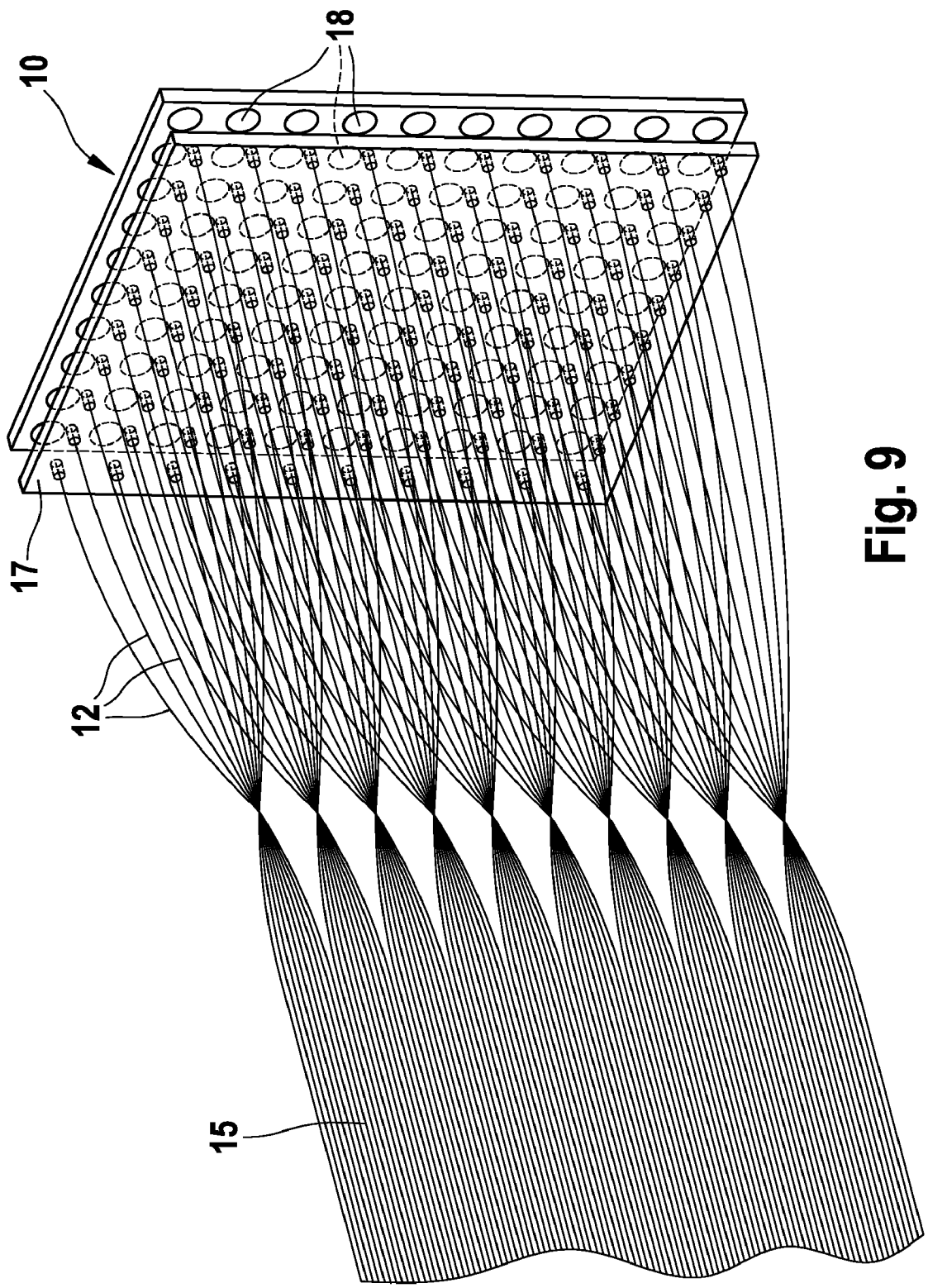
FIG. 9 shows a micro-lens array with a network of optical fibres, which can be used in an optical imaging detector according to the invention.

FIG. 9 shows a micro-lens array, which can be used for the present invention, with each micro-lens being connected to an optical fibre.

The micro-lens array 10 (in a square pattern) contains a multi-hole plate 17 and a plurality of mounted micro-lenses 18. A network of optical fibres 12 is mounted on the multi-hole plate 17 such that the focal points of the individual micro-lenses 18 correspond locally to single fibre ending points. The optical fibres merge into a fibre bundle 15.

Figure 10:
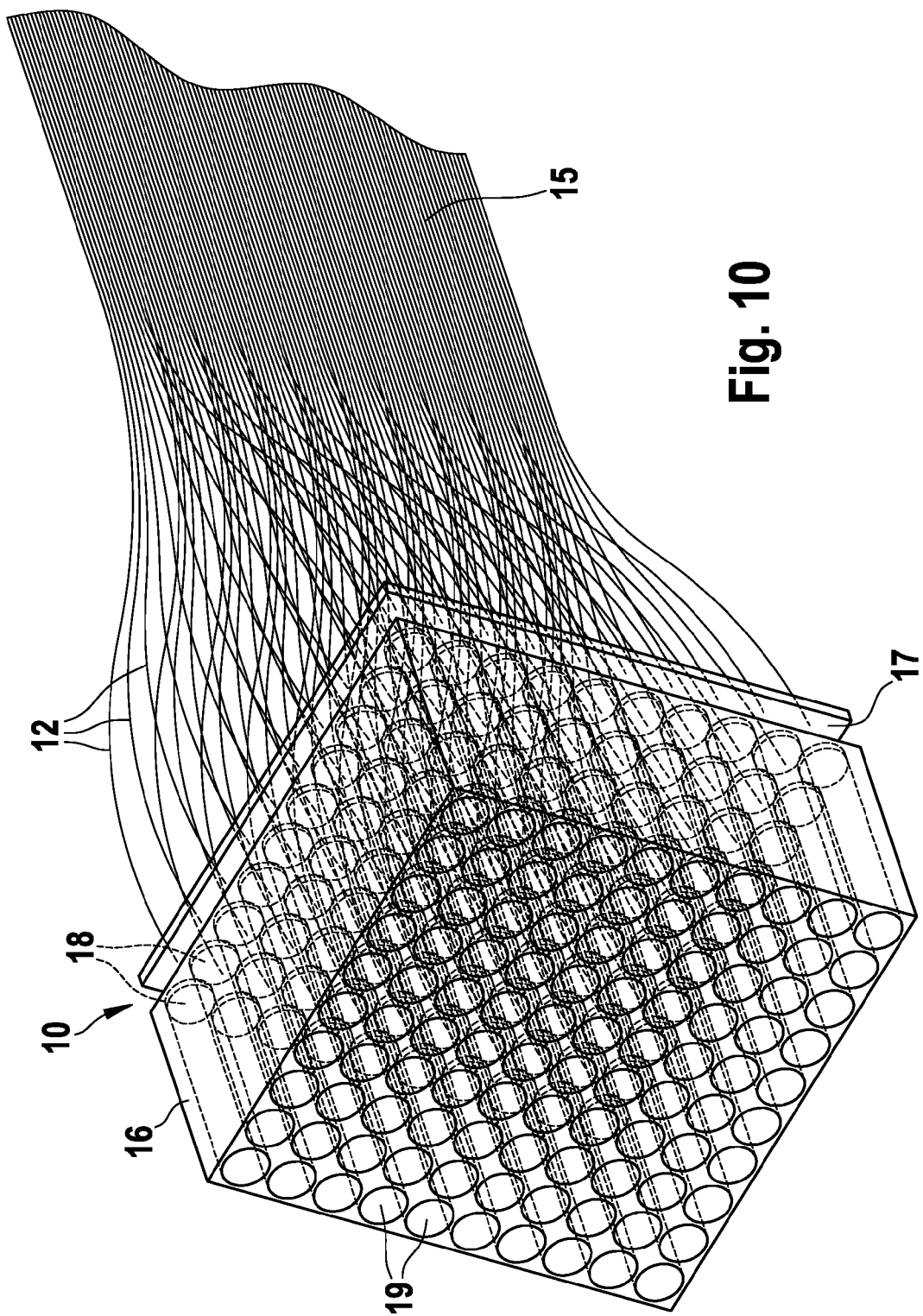
FIG. 10 shows a micro-lens array with an optical collimator, which can be used in an optical imaging detector according to the invention.

FIG. 10 shows a micro-lens array with an optical collimator.

In addition to the fibre bundles 15, the optical fibres 12, multi-hole plate 17, and micro-lenses 18, FIG. 10 shows a multi-hole collimator 16, which is mounted in front of the micro-lenses 18, each hole 19 of the collimator 16 corresponding to one micro-lens 18.

LIST OF REFERENCE NUMERALS

5 Imaged object
6 γ-ray detector arrays
7 Ring form
10 Micro-lens arrays
11 Ring structure
12 Optical fibres
13 Spaces
14 Electrical connection
15 Fibre bundles
16 Optical collimator
17 Multi-hole plate 18 Micro-lenses
19 Hole
20 Detector block
21 Micro-lens array
22 Micro-lenses
23 Filter
24 Optical collimator
25 Photo detector
26 Electronics parts and signal transmission elements
27 Imaged object
28 Light sources
29 Light ray
30 Gaps

The invention claimed is:

1. An optical imaging detector for fluorescence and bioluminescence imaging of an object to be imaged, the optical imaging detector comprising:
at least one micro-lens array with a plurality of micro-lenses, which are arranged to map light emitted from the imaged object, and
an optical detector having at least one photo detector, which comprises a two-dimensional lattice of pixels and is arranged to receive mapped light,
wherein the micro-lenses of the micro-lens array are arranged at a first pitch and pixels of the at least one photo detector are arranged at a second pitch, said first pitch is at least two times said second pitch.

2. The optical imaging detector according to claim 1, wherein each micro-lens has a diameter in a range from 0.1 to 2 mm.

3. The optical imaging detector according to claim 1, wherein the optical imaging detector is a non-contact detector.

4. The optical imaging detector according to claim 1, wherein the optical imaging detector comprises at least one photo detector.

5. The optical imaging detector according to claim 4, wherein the at least one photo detector comprises at least one CCD camera.

6. The optical imaging detector according to claim 4, wherein the at least one photo detector is a position sensitive photo detector.

7. The optical imaging detector according to claim 6, wherein the position sensitive photo detector is at least one sensor selected from the group of CCD based detector, APD array, photo diode array or CMOS sensor.

8. The optical imaging detector according to claim 6, wherein the at least one position sensitive photo detector is positioned at a focal plane of one of the micro-lens arrays.

9. The optical imaging detector according to claim 1, wherein each micro-lens is connected to an optical fibre.

10. The optical imaging detector according to claim 9, wherein each micro-lens is connected to a photo detector or to a light source via the optical fibre.

11. The optical imaging detector according to claim 1, wherein the at least one micro-lens array has a square, rectangular or hexagonal pattern of packed micro-lenses.

12. The optical imaging detector according to claim 1, comprising at least two opposed micro-lens arrays.

13. The optical imaging detector according to claim 1, wherein a plurality of planar or curved micro-lens arrays is arranged in a ring structure.

14. The optical imaging detector according to claim 1, wherein the optical imaging detector is mounted on a rotatable gantry.

15. The optical imaging detector according to claim 1, comprising at least one light source arranged to illuminate at least part of the imaged object.

16. The optical imaging detector according to claim 15 comprising at least one filter in front of each micro-lens array for filtering out light of the at least one light source.

17. The optical imaging detector according to claim 1, wherein the optical imaging detector is radially relocatable.

18. The optical imaging detector according to claim 1, wherein a pitch of an optical collimator included in said optical imaging detector corresponds to a pitch of the micro-lens array.

19. The optical imaging detector according to claim 1, wherein said light mapping of said imaging detector maps a defined field of view onto a defined point of a sensing surface, whereby said sensing surface corresponds to multiple points in said field of view.

20. The optical imaging detector according to claim 1, wherein an optical collimator is arranged next to each micro lens array.

21. A method for non-contact 3-dimensional optical imaging of an object to be imaged, said method comprising:
providing an optical imaging detector comprising a plurality of micro-lens arrays and a plurality of optical detectors,
acquiring imaging data of the imaged object by an with said optical imaging detector,
said plurality of micro-lens arrays and said plurality of optical detectors are arranged in a ring structure surrounding the imaged object in order to acquire light emitted from the imaged object from multiple projection views simultaneously,
wherein a plurality of micro-lenses of the plurality of micro-lens arrays map light emitted from the imaged object onto said plurality of optical detectors,
said plurality of optical detectors have at least one photo detector which comprises a two-dimensional lattice of pixels arranged to receive mapped light, and
wherein the micro-lenses of the micro-lens array are arranged at a first pitch and pixels of the at least one photo detector are arranged at a second pitch, said first pitch is at least two times said second pitch.

22. The method for non-contact 3-dimensional optical imaging according to claim 21, wherein a pitch of an optical collimator included in said optical imaging detector corresponds to a pitch of a micro-lens array from said plurality of micro-lens arrays.

23. The method for non-contact 3-dimensional optical imaging according to claim 21, wherein said mapping of light maps a defined field of view onto a defined point of a sensing surface of said plurality of optical imaging detectors, whereby said sensing surface corresponds to multiple points in said field of view.

24. The method for non-contact 3-dimensional optical imaging according to claim 21, wherein an optical collimator is arranged next to each micro lens array.

* * * * *

UNITED STATES PATENT AND TRADEMARK OFFICE
CERTIFICATE OF CORRECTION

| | |
|---|---|
| PATENT NO. | : 8,227,754 B2 |
| APPLICATION NO. | : 11/918857 |
| DATED | : July 24, 2012 |
| INVENTOR(S) | : Jorg Peter et al. |

It is certified that error appears in the above-identified patent and that said Letters Patent is hereby corrected as shown below:

ON THE TITLE PAGE:

At item (73), Assignee, change "Deutsches Krebforschungszentrum Stiftung Des Oeffentlichen Rechts, Heidelberg (DE)", to --Deutsches Krebsforschungszentrum Stiftung des oeffentlichen Rechts, Heidelberg (DE)--.

Signed and Sealed this
Thirteenth Day of November, 2012

David J. Kappos
*Director of the United States Patent and Trademark Office*